(12) United States Patent
Galesso et al.

(10) Patent No.: US 9,808,482 B2
(45) Date of Patent: Nov. 7, 2017

(54) SULPHATED HYALURONIC ACIDS AS REGULATOR AGENTS OF THE CYTOKINE ACTIVITY

(75) Inventors: Devis Galesso, Abano Terme (IT); Anna Maria Zanellato, Abano Terme (IT)

(73) Assignee: FIDIA FARMACEUTICI S.p.A., Abano Terme (IT)

( * ) Notice: Subject to any disclaimer, the term of this patent is extended or adjusted under 35 U.S.C. 154(b) by 0 days.

(21) Appl. No.: 13/320,015

(22) PCT Filed: May 11, 2010

(86) PCT No.: PCT/EP2010/003044
§ 371 (c)(1),
(2), (4) Date: Jan. 4, 2012

(87) PCT Pub. No.: WO2010/130466
PCT Pub. Date: Nov. 18, 2010

(65) Prior Publication Data
US 2012/0101059 A1 Apr. 26, 2012

(30) Foreign Application Priority Data
May 14, 2009 (IT) .............................. PD2009A0135

(51) Int. Cl.
*A61K 31/737* (2006.01)
(52) U.S. Cl.
CPC ................................ *A61K 31/737* (2013.01)
(58) Field of Classification Search
None
See application file for complete search history.

(56) References Cited

U.S. PATENT DOCUMENTS

| | | | | |
|---|---|---|---|---|
| 5,827,834 | A * | 10/1998 | Falk et al. ........................ | 514/54 |
| 6,051,701 | A * | 4/2000 | Cialdi et al. ..................... | 536/123 |
| 7,431,920 | B2 * | 10/2008 | Liu ......................... | A61K 38/21 424/85.2 |
| 2003/0162732 | A1 | 8/2003 | Weidner | |
| 2007/0054878 | A1 * | 3/2007 | Venbrocks ............ | A61K 31/728 514/54 |
| 2009/0197807 | A1 * | 8/2009 | Callegaro ............ | A61K 31/737 514/1.1 |

FOREIGN PATENT DOCUMENTS

| | | | |
|---|---|---|---|
| EP | 0754460 A1 | 1/1997 | |
| EP | 0889055 A1 | 1/1999 | |
| EP | 2090308 A1 | 8/2009 | |
| IT | WO 2009013162 A1 * | 1/2009 | .......... A61K 31/728 |
| JP | 11147901 A | 6/1999 | |
| JP | 11269077 A | 10/1999 | |
| JP | 2000178196 A | 6/2000 | |
| JP | 2001163789 A | 6/2001 | |
| WO | WO-95/25751 A1 | 9/1995 | |
| WO | WO-0232407 A2 | 4/2002 | |
| WO | WO-2005039528 A2 | 5/2005 | |
| WO | WO-2006128618 A1 | 12/2006 | |

OTHER PUBLICATIONS

Akdis et al. Diagnosis and treatment of atopic dermatitis in children and adults: European Academy of Allergology and clinical Immunology/American Academy of Allergy, Asthma and Immunology/PRACTALL Consensus Report. Allergy, 61, 2006, pp. 969-987.*
Ong, P. Y., & Leung, D. M. (2006). Immune dysregulation in atopic dermatitis. Current allergy and asthma reports, 6(5), 384-389.*
Corsini, E., & Galli, C. L. (1998). Cytokines and irritant contact dermatitis. Toxicology Letters, 102, 277-282.*
Nishimoto, N. (2006). Interleukin-6 in rheumatoid arthritis. Current opinion in rheumatology, 18(3), 277-281.*
Boyle, W. J., Simonet, W. S., & Lacey, D. L. (2003). Osteoclast differentiation and activation. Nature, 423(6937), 337-342.*

* cited by examiner

*Primary Examiner* — Shaojia Anna Jiang
*Assistant Examiner* — Dale R Miller
(74) *Attorney, Agent, or Firm* — Birch, Stewart, Kolasch & Birch, LLP (57) ABSTRACT

The object of the present invention relates to the new and surprising use of sulfated hyaluronic acid (HAS) as regulator agent of the cytokine activity (pro- and anti-inflammatory) and consequently the use of HAS for the preparation of a new medicine for the prevention and treatment of pathologies associated with the activation and/or deficiency of cytokines of a pro- and anti-inflammatory nature. The Applicant has in fact discovered its exclusive capacity in modulating the activity of these particular proteins, it has studied the action mechanism and demonstrated the substantial difference between the different sulfated types known in the state of the art, but above all it has demonstrated an unexpectedly high activity of HAS vs different types and strains of Herpes virus, HIV, Cytomegalovirus and the virus of vesicular stomatitis.

4 Claims, 6 Drawing Sheets

| Product tested | Minimum inhibitory concentration IC 50 (µg/ml) | |
|---|---|---|
| | HIV-1 (III_B Strain) | HIV-2 (ROD Strain) |
| HA -NS1 | >125 | >250 |
| HAS1 | 2,3 | 14,4 |
| HAS3 | 0,15 | 0,66 |
| | | |
| DS | 0,135 | 0,025 |

Fig. 11

| Product tested | Minimum Cytotox. concentration (µg/ml) | Minimum inhibitory concentration IC 50 (µg/ml) | | | | | | |
|---|---|---|---|---|---|---|---|---|
| | | Herpes simplex virus-1 (KOS) | Herpes simplex virus-1 (F) | Herpes simplex virus-1 (McIntyre) | Herpes simplex virus-2 (G) | Herpes simplex virus-2 (196) | Herpes simplex virus-2 (Lyons) | Vesicular stomatitis virus |
| HA-NS1 | >400 | >400 | >400 | >400 | >400 | >400 | >400 | >400 |
| HAS1 | >400 | 48 | 16 | 9,6 | 9,6 | 3,2 | 3,2 | 1,92 |
| HAS3 | >400 | 16 | 3,2 | 1,92 | 1,92 | 1,92 | 1,92 | 0,128 |
| | | | | | | | | |
| DS | >400 | 9,6 | 9,6 | 9,6 | 3,2 | 3,2 | 1,92 | 16 |
| Acyclovir | >400 | 0,384 | 0,384 | 0,64 | 0,384 | 0,384 | 0,384 | >80 |

Fig. 12

| Product tested | Minimum inhibitory concentration IC 50 (µg/ml) | |
|---|---|---|
| | Cytomegalovirus AD-169 strain | Cytomegalovirus Davis strain |
| HA-NS1 | >50 | >50 |
| HAS1 | 5 | 3,4 |
| HAS3 | 0,2 | 0,2 |
| | | |
| DS | 2,7 | 0,5 |

SULPHATED HYALURONIC ACIDS AS REGULATOR AGENTS OF THE CYTOKINE ACTIVITY

This application is the National Phase under 35 U.S.C §371 of PCT International Application Number PCT/EP2010/003044 which has an International filing date of May 11, 2010, which claims priority to Italian Application Number PD2009A000135 filed on May 14, 2009. The entire contents of all applications listed above are hereby incorporated by reference.

FIELD OF THE INVENTION

For many years now, scientific/patent literature has been studying and describing sulfated hyaluronic acid which is obtained starting from hyaluronic acid (HA) suitably sulfated according to what is described in the state of the art (EP0940410B1 and EP0702699B1), to which anticoagulant effects are attributed. HAS can also be obtained by the de-acetylation and subsequent sulfation of glucosamine of HA (defined as HA-NS) (EP0971961B1), for the production of surgical articles and pharmaceutical compositions. Patents EP0754460B1 and EP1385492B1 are also known, in which the use of HAS is described in pathologies such as, for example, ARDS, articular rheumatism, rheumatoid arthritis and dermatitis.

An object of the present invention relates to the new and surprising use of HAS as regulator agent of the cytokine activity, as the Applicant has discovered the exclusive capacity of HAS of modulating the activity of particular cytokines (both pro- and anti-inflammatory), it has studied its action mechanism and revealed the substantial difference between the two types of sulfated product (HAS and HA-NS), but above all the Applicant has surprisingly found an unexpectedly high activity vs different types and strains of Herpes virus, HIV, Cytomegalovirus and the virus of vesicular stomatitis.

Since 1970, scientists have understood that selected populations of lymphoid cells can produce and release into the circulatory bed, molecules of a protein nature not assimilable to antibodies, defined with the term "cytokines". They represent a new type of "hormone", capable of acting on different cell targets in numerous regions of the body.

The progression of scientific knowledge relating to the synthesis and biological/biochemical functions of these proteins, has altered the "old" vision of the immune system (I.S.) of the same scientific world and has opened up new horizons in understanding its numerous functions, thus creating new prospects for the treatment of different pathologies, topic and/or systemic, also comprising new therapeutic possibilities relating to the immunotherapy of cancer.

The central IS cell is the lymphocyte, it represents about 20% of all the white blood cells and, on the basis of its various functions, forms 3 groups: lymphocyte B, lymphocyte T and killer lymphocyte. Many cytokines are soluble proteins produced by lymphocytes and/or monocytes, capable of acting against other cells/tissues also situated very far from their production site. They have immunological functions, in fact, and also regulation functions in the synthesis of other cytokines by different cells of the I.S. or target cells involved in the cascade of reactions initiated by the I.S.

Numerous different cytokines have been studied so far, also having numerous different acronyms, but those studied in particular by the Applicant are: Interleukin 1 and 2, Interleukin 6, 7 and 12, hereafter defined as IL-1, IL-2, IL-6, IL-7 and IL-12 which, with TNF, are defined as cytokines of a pro-inflammatory nature, whereas Interleukin 10 (IL-10) on the contrary, is a cytokine with strong anti-inflammatory properties.

The first cytokine to be studied was definitely IL-1 present in two forms $\alpha$ and $\beta$, a powerful inducer of inflammatory processes, both local and systemic. It is mainly produced by lymphocytes B; T and macrophages after bacterial stimulus or stimulation on the part of other agents including other cytokines; it is also secreted from alveolar, peritoneal macrophages, Kupffer cells, peripheral neutrophils, endothelial, epithelial and smooth muscle cells, fibroblasts, Langerhans cells of the skin, osteoclasts, synoviocytes and many other types of cell. It is also present in the cerebrospinal fluid where it is both produced and transported. Both forms bind the same receptor and have very similar, if not identical, biological activities. Many of their pro-inflammatory functions are linked to the stimulation of other cytokines, such as IL-6 and IL-8, and their very synthesis can be induced by cytokines such as TNF, Interferon, bacterial endotoxins, viruses and different types of other antigens. It is involved in septic shock but it should also be noted that recent studies have demonstrated that IL-1 is capable of activating the expression of some oncogenes and consequently of participating in the pathogenesis of neoplasias. Furthermore, an autocrin control system of the growth of blast cells of the white series which are present in the circulatory bed of patients with the leukaemia pathology has been suggested for this cytokine: these blast cells in fact uncontrollably produce IL-1 which in turn stimulates the synthesis of those growth factors which increase the proliferation of the same blast cells. Combined with other cytokines, IL-1 therefore represents one of the major mediators of inflammatory processes: it stimulates T-cells in fact to produce IL-2 and B-cells to produce immunoglobulins. It is consequently involved in numerous pathologies such as, for example, astrogliosis and the demyelination of neuronal fibres, it is cytotoxic for Langerhans pancreatic cells which produce insulin, and is also involved in lithic processes of the bones, both activating osteoclasts and suppressing the formation of new bone, both processes being involved in the pathology of osteoporosis. It is capable of functioning as an endogenous pyrogen as, by increasing the release of prostaglandins in the hypothalamic centre, it causes an increase in the body temperature. It is also involved in the pathogenesis of rheumatoid arthritis and arthrosis: high quantities of IL-1 have in fact been found in the synovial fluid of patients affected by rheumatoid arthritis and/or osteoarthrosis. Finally, it participates in the establishment of vascular damage such as venous thrombosis and is present in all vessels with pathologies of the arterio/arterioschlerotic type. Receptor antagonists are currently being experimented for this cytokine, as blockage of the receptor is proving to be an effective way of treating these pathologies in which IL-1 is among the protagonists.

TNF: The necrosis factor is part of the group of cytokines which promotes the reaction of acute systemic inflammation phase. TNF is therefore involved in an extremely wide number of processes such as cell proliferation, differentiation and apoptosis, carcinogenesis and viral replication.

It is mostly produced by macrophages and by a series of other cell types including mastocytes, lymphoid cells, muscular and endothelial cells, fibroblasts and nerve cells. Its synthesis can be stimulated by bacterial endotoxins, other cytokines such as IL-2, Interferon and IL-1, and it can be inhibited by steroids.

By acting on numerous organs and systems, generally together with other cytokines, it participates in the establishment and regulation of many pathogenetic processes:

- it modulates the expression of many proteins and important cytokines, such as IL-1 and IL-6 thus resulting involved in many cutaneous pathologies such as, dermatitis, vitiligo and eczema;
- it stimulates the hypothalamo-hypophyseal-adrenal axis increasing the release of some types of hormones;
- it suppresses the appetite;
- it induces fever (it acts as endogenous pyrogen inducing the hypothalamus to produce prostaglandins);
- it stimulates the synthesis of collagenasis in the synoviocytes and for this reason, large quantities of TNF have been found in the synovial fluids of patients suffering from arthrosis and rheumatoid arthritis;
- it activates the osteoclasts and therefore induces re-absorption of the bone, process characterizing the osteoporosis pathology;
- it is also involved in pathologies of the Nervous System, such as astrocytosis and demyelination;
- it strongly attracts neutrophils and helps them attach themselves to the endothelial cells to extravasate;
- it stimulates the macrophagic production of molecules with an oxidizing action;
- it is involved in particular pathologies of the Cardio-circulatory System participating in the formation of venous thrombosis, in the pathogenesis of arteriosclerosis and vasculitis;
- it increases the resistance to insulin, it increases the protein catabolism in the muscles whereas it suppresses the lipogenic metabolism in the adipose tissue.

High concentrations of TNF can induce shock-like symptoms, whereas prolonged exposure to low concentrations can lead to cachexia, a syndrome which causes the depletion of the protein and lipid patrimony of the tissues (in particular muscular and adipose). The TNF is capable of binding itself to two receptors, TNF-R1 (receptor for type 1 TNF) and TNF-R2 (receptor for type 2 TNF), which are expressed in all somatic cells excluding erythrocytes. In short, the TNF promotes the inflammatory response which in turn triggers numerous pathologies also of an auto-immune nature, such as rheumatoid arthritis, Crohn disease, psoriasis and asthma. Scientific research has so far tried to perfect "biological" drugs (such as, for example, monoclonal antibodies) which inhibit the synthesis of TNF and/or block its receptor.

IL-2: this is a highly pro-inflammatory, atherogenic cytokine, mainly produced by lymphocytes T, whose synthesis is inhibited by steroids and cyclosporines. Leukemic cells synthesize the above cytokine and contemporaneously express its receptor, thus creating an autocrin system in the stimulation of their growth which causes a deterioration in the leukemia pathology. IL-2 has a central role in regulating the immunological response: it stimulates in fact the synthesis of IFN in the peripheral leukocytes and induces the production of IL-1 and TNF. IL-2 can also damage the hematoencephalic barrier and integrity of the endothelium of the cerebral vessels, causing neuropsychiatric disorders such as disorientation and depression.

There are consequently numerous pathologies which have been associated with an aberrant production of IL-2, such as Hodgkin's lymphoma, the rejection of organ transplants, multiple sc(h)lerosis, rheumatoid arthritis, Lupus erythematosus, diabetes and AIDS.

IL-6: produced by many cell types above all of I.S., with TNF it is amongst the most important members of the group of chemical mediators of the acute phase of the inflammatory process, and is therefore involved in pathologies with a strong inflammatory component, such as asthma (where it participates in the emergence and maintenance of the inflammatory process), chronic intestinal inflammation (Crohn's disease), rheumatoid arthritis and arthrosis. As previously affirmed, in fact, cytokines such as TNF, IL-1 and IL-6 have proved to be greatly involved in the degenerative articular osteoarthrosis process as they have a primary role in regulating the expression of metalloproteases (responsible for cartilage degradation), in the production of prostaglandins and in osteoclastic activation and, for this reason, high cytokine levels have been registered in the synovial fluids of patients suffering from arthrosis and rheumatoid arthritis (R.A.). These discoveries have stimulated the use of inhibitors in the above interleukins and/or receptor antagonists as a new treatment strategy of the arthrosis pathology.

High concentrations of IL-6 have also been found in the urine of patients subjected to transplants and its presence represents one of the first signs of the rejection reaction of the organ. The serum level of this cytokine is also drastically increased in many patients suffering from tumors (such as, for example, myeloma, leukemia, cardiac myxomas, or in pathologies such as lymphadenopathies and hepatic cirrhosis) and can also be used as indicator in monitoring the size of the tumoral mass. Finally, recent studies have connected cancer with longevity and revealed how some tumors are influenced by the quali/quantitative situation of the cytokine proteins of the patient: in short, recent evidence has linked a low production profile of IL-10 and high secretion of IL-6 to a deterioration in the clinical survival of patients affected by tumoral pathologies, whereas a genotype capable of producing and maintaining high levels of IL-10 can facilitate survival. Consequently, persons with high anti-inflammatory cytokine levels and a low concentration of pro-inflammatory cytokines are genetically susceptible to having a greater longevity (Caruso C. et al., Ann N.Y. Acad. SCI., 2004, 1028:1-13).

IL-7; cytokine mainly produced by stromal cells of bone marrow, it is also secreted by the thymus and keratinocytes. IL-7 induces the synthesis of inflammatory cytokines such as IL-1, IL-6 and TNF, thus participating in the pathogenesis of some skin diseases (such as psoriasis and cutaneous lymphoma) and the osteoarticular system. High levels of IL-7 have in fact been found in patients suffering from R.A. as IL-1 and TNF (cytokines strongly involved in the above pathology) can increase the stromal production of IL-7 which in turn stimulates the macrophagic synthesis of TNF. Finally, IL-7 can induce the maturation of osteoclasts and consequently increase bone resorption thus contributing to the degeneration of the joints.

IL-12: this protein also plays a central role in regulating the functions of the I.S. It acts in fact on the differentiation of the lymphocytes, it induces the synthesis of Interferon and TNF, and its production can be inhibited by IL-10. The overproduction of this protein enters in the pathogenesis of diseases of (an) auto-immune nature such as colitis, arthritis, insulin-dependent diabetes, encephalomyelitis, psoriasis and multiple schlerosis (Brahmachari S. et al., Minerva Med., 2008, 99(2):105-118).

IL-10: mainly produced by lymphocytes, it is a cytokine of an anti-inflammatory nature, capable of inhibiting the synthesis of IL-2 and Interferon produced by lymphocytes T. The anti-inflammatory action of IL-10 is also revealed in the capacity of inhibiting the synthesis of IL-1, IL-6, IL-8, IL-12 and TNF in the macrophages stimulated with bacterial endotoxins. IL-10 deficiencies are associated with pathologies such as diabetes mellitus and chronic intestinal inflammations, such as Crohn's disease. Recent evidence has led IL-10 to also be experimented as a new therapeutic approach for the treatment of Lupus erythematosus. Low IL-10 levels have been observed in cutaneous tissues of patients suffering of pathologies such as vitiligo, psoriasis, eczema and dermatitis in general. It should be noted that both corticosteroids and cyclosporine increase the production and/or release of this interleukin from the relative competent cells during conventional immunosuppression therapy for the treatment of inflammations and organ rejection (Zhou X. Et al., Current Drug Targets-Immune, Endocrine & Metabolic Disorders, 2005, 5(465475). Experimental data have also demonstrated its effectiveness in reducing the release of prostaglandins and cyclo-oxygenase induced in vitro by TNF on human synoviocytes, thus indicating the capacity of IL-10 of reducing inflammatory processes which involve articulations affected by osteoarthrosic degeneration (Alaaeddine N. et al., Arthritis & Rheumatism, 1999, 42:710-718). Recent studies have confirmed its therapeutic effectiveness towards the asthma pathology in experimental animal models of bronchial hyper-reactivity, showing how this cytokine has a high therapeutic potentiality in reducing the inflammation which characterizes the air passages of asthmatic patients, in which high concentrations of TNF, IL-1, IL-5, IL-6 and IL-8 have been found in the bronchial-washing liquid and/or on a serum level and/or tissue level (Stankiewicz W. et al., Mediators of Inflammation, 2002, 11:307-312). For this interleukin, the important role of regulator cytokine of the maintenance of immunological homeostasis, has therefore been assumed.

Asthma can be an extremely invalidating disease of which approximately 200 million people in the world suffer, with over 5,000 deaths per year. It is a pathology which is based on a distorted response of the I.S. to environmental factors, consequently linked to an exacerbated production of pro-inflammatory cytokines for the growth and differentiation of mast cells and eosinophils with other types of cells of the I.S. The causes of this out-of-balance activity of the immune system are still not completely known, there are however genetic, environmental, viral and also nutritional factors which contribute in different ways to the development of this pathology. Consequently, finding an effective therapy for its prevention and/or treatment which allows the suspension or reduction of the use of steroids (conventional treatment therapy), could represent a valid solution for both the more serious forms (as it would in any case enable a reduction in the use of steroids) and for less serious cases, as the suspension of the steroid therapy could be total.

DETAILED DESCRIPTION OF THE INVENTION

An object of the invention is the new and surprising use of HAS as regulator agent of the cytokine activity, as the Applicant has discovered its exclusive capacity in modulating the activity of particular cytokines, it has studied its action mechanism and revealed the substantial difference between the various types of sulfated products known in the state of the art, but above all the Applicant has discovered an unexpected activity vs different types and strains of Herpes virus, HIV, Cytomegalovirus and the virus of vesicular stomatitis. The sulfated hyaluronic acid suitable for the purposes of the present invention is prepared according to the process described in EP 702699 B1: the sulfation is effected by means of the complex $SO_3$-pyridine and involves the alcohol hydroxyls present in the polysaccharide chain starting from a HA deriving from any source, for example, by extraction from cockscombs, either fermentatively or technologically, and having a molecular weight ranging from 400 to $3\times10^6$ Da, in particular from $1\times10^4$ Da to $1\times10^6$ Da, even more in particular from 10,000 to 50,000 Da, 150,000 to 250,000 Da and 500,000 to 750,000 Da.

The derivative obtained maintains all the physical characteristics of the starting polymer unaltered, in particular the molecular weight of the starting HA is not altered by the sulfation process thus allowing all the physico-chemical characteristics of the starting polysaccharide to be maintained. The sulfation involves the various hydroxyl groups of the disaccharide unit and it is therefore possible to obtain different sulfation degrees, from 0.5 to 3.5 (intended as the number of sulfate groups per disaccharide unit), by varying the quantity of $SO_3$-pyridine introduced as known in the state of the art.

The derivative used in all the experimentations effected generally has sulfation degree 1 or degree 3 and is defined hereafter as HAS1 and HAS3. All the free carboxyl groups of the HA can be salified with cations of an organic and/or inorganic origin.

Both degrees of HAS are soluble in water and they can also be sterilized with the normal techniques known to experts in the field, even if sterilization using an autoclave is preferable.

In the experimentations described hereunder, the Applicant demonstrated that:

HAS is capable of both stimulating the production of new mRNA and the protein synthesis of anti-inflammatory cytokines (such as, for example, IL-10), thus increasing the immune defense capacity of the cells and therefore of the whole organism. The anti-inflammatory action of the above cytokines is revealed in the capacity of inhibiting the synthesis of IL-1, IL-6, IL-8, IL-12 and TNF, all proteins of a pro-inflammatory nature.

HAS is effective in both diminishing the synthesis of new mRNA and in significantly reducing the protein synthesis of IL-2, IL-7 and IL-12 on the part of the synoviocytes (for IL-12) and cell components of the I.S., both in situations in which an immune response is not demanded, and also in particular inflammatory stress events in which the immune cell responds by producing a cytokine cascade and, above all in this case, the data presented reveal the greater inhibitory effect of HAS.

HAS is effective in inhibiting the binding of TNF, IL-1 and IL-6 to their receptor. These results are of fundamental importance as they prove that the behaviour of the sulfate is completely similar to that of specific monoclonal antibodies for the receptors of the above pro-inflammatory proteins, consequently capable of blocking their function even if they do not have this specificity. This receptor blockage represents the most effective way of antagonizing the pro-inflammatory and tumoral effects of the TNF, IL-1 and IL-6 factor, thus opening up new horizons in clinical experimentation, allowing the perfectioning of new therapeutic approaches in the treatment and/or prevention of an extremely high number of pathologies, considering the role that TNF, IL-1 and IL-6 have in the onset and progression of numerous diseases.

The Applicant therefore describes and claims the new use of HAS for the preparation of a medicine:
- for the prevention and/or treatment of pathologies associated with immune deficiency and, in particular, deficiency of IL-10, stimulating the synthesis of anti-inflammatory cytokines as new local and systemic therapy of pathologies such as vitiligo, eczema, psoriasis and dermatitis;
- for the prevention and/or treatment of pathologies associated with the increase/activation of IL-1, IL-2, IL-6, IL-7, IL-8, IL-12 and TNF;
- for the prevention and/or treatment of asthma, rheumatold arthritis, and arthrosis associated with the activation of IL-1, IL-6 and TNF;
- for the prevention and/or treatment of pathologies associated with endothelial damage in blood vessels;
- for the prevention and/or treatment of skin diseases such as, for example, dermatitis and cutaneous lymphoma;
- for the prevention and/or treatment of diseases of an autoimmune nature such as rheumatoid arthritis, Crohn's disease (and all chronic intestinal inflammations), psoriasis and asthma, diabetes mellitus, encephalomyelitis, Multiple Sclerosis, Lupus erythematosus and for the treatment of rejection in organ transplants;
- for the prevention and/or treatment of neoplasias such as, for example, leukaemia and Hodgkin's lymphoma;
- for the prevention and/or treatment of astrogliosis, astrocytosis and demyelination of the neuronal fibres;
- for the prevention and/or treatment of pathologies associated with the activation of osteoclasts, such as the osteoporosis;
- for the prevention and/or treatment of vascular pathologies of the arterio/atheroschlerotic type, venous thrombosis and vasculitis, associated with the activation of TNF, IL-1 and IL-6;
- for the prevention and/or treatment of febrile pathologies.

The Applicant has also demonstrated, in the experimentations described hereunder, the powerful antiviral action of HAS vs different types of viruses:
- the results obtained show the effectiveness of HAS (both degree 1 and degree 3) in inhibiting the viral replication of the HIV 1 and 2 virus. The experimentation has also demonstrated that not all sulfated hyaluronic acids known in the state of the art act effectively vs viral replication, as only HAS in which the sulfation has taken place with respect to the hydroxyl groups alone has proved to be active, where HA-NS is not effective in blocking viral cytopathogenicity.

Experimental data confirm the antiviral action of HAS1 and HAS3 vs Herpes Simplex virus 1 and 2 and vs the virus of vesicular stomatitis (VSV). The first form, extremely widespread, is responsible for the appearance of characteristic febrile vesicles which normally affect the facial cutis (lips, nostrils); it is also called herpes simplex labialis. The infection caused by lip herpes can easily reappear as the virus survives inside the cells and is not even eliminated with the use of effective drugs. The second form is a genital infection, also known as herpes genitalis. Both are caught by physical and sexual contact. Due to the location of the virions in the nervous ganglia, where they can remain quiescent for a long period of time, the herpetic infection has recurring characteristics in correspondence with stressing events of the immune system and usually reappears in the primary site. The virus of vesicular stomatitis is an RNA-virus, it strikes mammals (mainly animals) and is used in the laboratory for studying the development of the life-cycle of the RNA-virus. A comparison between HA-NS1 and HAS1 shows once again that not all sulfated hyaluronic acids are equivalent, as HA-NS1 has proved not to be active at all, whereas both HAS 1 and 3 show a very strong anti-viral activity vs Herpes Simplex and also vs VSV. None of the samples tested prove to be cytotoxic towards the host cell, the minimum cytotoxic concentration obtained, in fact, is equal to that of reference drugs normally used in clinical practice for the treatment of Herpes, and on an average has proved to be 100 times higher than that revealed active in the inhibition of viral replication.

Experimental data obtained for both HAS1 and HAS3 have revealed a clear and significant antiviral result vs Cytomegalovirus: this is a particular type of virus which enters some types of cells of our organism in which it reproduces itself parasitically causing their death. It belongs to the same family as herpes labialis and herpes genitalis, chickenpox and infective mononucleosis. Epithelial cells, mucous membranes, lymphonodes are the site of multiple primary infection. It remains in latent form for life in the peripheral blood, in the epithelium of the renal tubules and in the epithelium of the salivary glands. Serious forms are found in immunocompromised subjects (such as those affected by AIDS and transplant subjects in immunosuppressive therapy) involving various organs: pneumonia, hepatitis, colitis, esophagitis, nephritis. The treatment therapy consists in the administration of drugs such as ganciclovir, valganciclovir and foscarnet (inhibitors of the synthesis of viral DNA). Also in this case, HA-NS1 has proved to be non-active in inhibiting the proliferation of the virus confirming the absolute diversity, as antiviral capacity, between the two types of sulfated products.

The Applicant therefore describes and claims the new use of HAS for the preparation of a medicine:
- for the prevention and/or treatment of HIV;
- for the prevention and/or treatment of herpes simplex labialis and herpes genitalis;
- for the prevention and/or treatment of the virus of vesicular stomatitis;
- for the prevention and/or treatment of Cytomegalovirus.

Finally, the Applicant describes the preparation of various pharmaceutical formulations/compositions containing HAS as sole active principle, or in association with other pharmacologically and/or biologically active agents such as, for example, steroids, hormones, proteins, trophic factors, vitamins, non-steroid anti-inflammatory drugs (FANS), chemotherapy drugs, calcium-antagonists, antibiotics, antiviral agents, anticoagulants and/or fibrinolytic agents, local anaesthetics, enzymes such as, for example, collagenase and/or hyaluronidase and/or other proteases; it can be formulated with polymers such as hyaluronic acid and its derivatives, carboxymethylcellulose and/or other polymers of a natural (such as collagen) or synthetic nature.

The pharmaceutical composition in question can be administered systemically (endovenously or arterially, intramuscularly, intraperitoneally, hypodermically or orally), it can be used for a topic application by dermal and/or transdermal absorption, it can be administered by inhalation/aerosol (especially for the treatment of asthmatic pathologies), intra-articularly or it can be administered directly in the site to be treated by direct injection.

The pharmaceutical composition in question can be formulated as an ointment, lipogel, hydrogel, lipstick, cream, vaginal ovules and bougies, foam, mucosal gel, ophthalmic preparations, douches, mouthwash, patches for dermal and/or transdermal absorption, especially of FANS and hormones, solution for inhalant use.

Some examples of the preparation of HAS degree 1 and 3, pharmaceutical formulations containing it, are provided for purely descriptive and non-limiting purposes, together with the results obtained by experimentation in vitro.

Example 1

Preparation of the Tetrabutylammonium Salt of Hyaluronic Acid (HA) Having an Average Molecular Weight Equal to 200 KD (ranging from 150,000 to 250,000 Da)

5.00 g of hyaluronic acid of a fermentative sodium salt origin (200 KD) were dissolved in 250 ml of water and the resulting solution was percolated through a glass column pre-filled with 100 cm$^3$ of Dowex resin in the form of tetrabutylammonium (TBA). The eluted solution of HA-TBA salt is collected and freeze-dried. 7.50 g of product are obtained.

Example 2

Synthesis of Sulfated HA Starting from HA Having an Average Molecular Weight of 200 KD and a Sulfation Degree Equal to 3 Sulfate Groups Per Repetitive Unit
Method A 10.0 g of the TBA salt of hyaluronic acid having an average molecular weight of 200 KD prepared according to Example 1, are dissolved in 300 ml of dimethylsulfoxide (DMSO); 26.0 g of the complex $SO_3$-pyridine (sulphur trioxide and pyridine, hereafter abbreviated as $PySO_3$) are dispersed in 150 ml of DMSO, and then added to the solution of HA. After 20 hours under mechanical stirring at a temperature of 21° C., the reaction is interrupted adding 0.1 volumes of water; the raw reaction product is isolated by precipitation after the addition of 2 volumes of ethanol. The solid obtained is dispersed in 150 ml of water and the pH brought to neutrality with NaOH 1M. The mixture is exhaustively dialysed against water through a membrane with a cut-off of 12-14,000 Da. The dialysed product is subjected to freeze-drying. 9.7 g of product are obtained with a sulfation degree equal to 3 sulfate groups per repetitive unit (yield=88%).

Method B 32.0 g of the TBA salt of hyaluronic acid having an average molecular weight of 200 KD prepared according to Example 1, are dissolved in 900 ml of N-Methyl-Pyrrolidone (NMP); 100 g of $PySO_3$ are dispersed in 600 ml of NMP, and then added to the solution of HA. After 20 hours under mechanical stirring at a temperature of 21±1° C., the reaction is interrupted adding 0.5 volumes of water; The pH initially lower than 2.5, is brought to neutrality with NaOH (in solution). The reaction raw product is isolated by precipitation by the addition of 2.5 volumes of methanol and washed with 2 volumes of a methanol/water mixture 8/2. The solid is re-dissolved and exhaustively dialysed against water through a membrane with a cut-off of 12-14,000 Da. 30.4 g of product are obtained with a sulfation degree equal to 3 sulfate groups per repetitive unit (yield=86%).

Example 3

Synthesis of Sulfated HA Starting from HA having an Average Molecular Weight of 200 KD and a Sulfation Degree Equal to 1 Sulfate Group Per Repetitive Unit Using the procedure illustrated in Example 1, 10.0 g of TBA salt of HA are prepared, which are dissolved in 350 ml of DMSO. 10.0 g of the complex $PySO_3$ are dispersed in 100 ml of DMSO, and then added to the solution of HA. After 20 hours under mechanical stirring at a temperature of 21° C., the reaction is interrupted adding 0.1 volumes of water; the raw reaction product is isolated by precipitation after the addition of 2.5 volumes of ethanol. The solid obtained is dispersed in 150 ml of water and the pH brought to neutrality with NaOH 1 moles/l. The mixture is exhaustively dialysed against water through a membrane with a cut-off of 12-14,000 Da. The dialysed product is subjected to freeze-drying. 7.54 g of product are obtained with a sulfation degree equal to 1.0 sulfate group per repetitive unit (yield=93%).

Example 4

Synthesis of Sulfated HA Starting from HA Having a Low Molecular Weight (Average MW of 10 KD, Ranging from 10,000 to 50,000 Da) and a Sulfation Degree Equal to 3 Sulfate Groups Per Repetitive Unit Using the procedure illustrated in Example 1, 12.4 g of TBA salt of low-molecular-weight hyaluronic acid are prepared, which are dissolved in 300 ml of NMP. 40 g of $PySO_3$ are dispersed in 100 ml of NMP, and then added to the solution of HA. After 20 hours under mechanical stirring at a temperature of 21° C., the reaction is interrupted adding 0.5 volumes of water. The pH initially lower than 2.5, is brought to neutrality with NaOH 4M. The reaction raw product is isolated by precipitation by the addition of 2.5 volumes of methanol and washed with 2 volumes of a methanol/water mixture 8/2. The solid is re-dissolved and exhaustively dialyzed against water through a membrane with a cut-off of 3,500 Da. 12.0 g of product are obtained with a sulfation degree equal to 3.0 sulfate groups per repetitive unit (yield=85%).

Example 5

Synthesis of Sulfated HA Starting from HA Having a low Average Molecular Weight and a Sulfation Degree Equal to 1 Sulfate Group Per Repetitive Unit Using the procedure illustrated in Example 1, 12.4 g of TBA salt of HA are dissolved in 300 ml of DMSO. 16.0 g of $PySO_3$ are dispersed in 100 ml of DMSO and then added to the solution of HA. After 20 hours under mechanical stirring at a temperature of 21° C., the reaction is interrupted adding 0.1 volumes of water; the reaction raw product is isolated by precipitation by the addition of 2.5 volumes of ethanol. The solid obtained is dispersed in 150 ml of water and the pH brought to neutrality with NaOH 1 moles/l. The mixture is exhaustively dialyzed against water through a membrane with a cut-off of 3,500 Da. The dialyzed product is subjected to freeze-drying. 9.04 g of product are obtained with a sulfation degree equal to 1.0 sulfate group per repetitive unit (yield=90%).

Example 6

Synthesis of Sulfated HA Starting from HA Having a Molecular Weight within the Range of 500-730 KD Da and a Sulfation Degree Equal to 3 Sulfate Groups Per Repetitive Unit 21.0 g of hyaluronic acid sodium salt of an extractive origin (500-730 KD) are dissolved in 1.5 l of water and the resulting solution is percolated through a glass column pre-filled with 450 cm$^3$ of Dowex resin in the form of TBA. The eluted solution of HA-TBA salt is collected and freeze-dried. 32.0 g of product are obtained, which are dissolved in 1.35 l of NMP; 100 g of PySO$_3$ are dispersed in 650 ml of NMP, and then added to the solution of HA. After 20 hours under mechanical stirring at a temperature of 23±1° C., the reaction is interrupted adding 0.5 volumes of water. The pH initially lower than 2.5, is brought to neutrality by the addition of NaOH (in solution at a concentration of 4 moles/l). The reaction raw product is isolated by precipitation by the addition of 2.5 volumes of methanol and washed with 3.5 volumes of a methanol/water mixture 8/2. The solid is re-dissolved and exhaustively dialyzed against water through a membrane with a cut-off of 12-14,000 Da. 30.3 g of product are obtained with a sulfation degree equal to 3 sulfate groups per repetitive unit (yield=83%).

Example 7

Synthesis of Sulfated HA Starting from HA Having a Molecular Weight within the Range of 500-730 KD and a Sulfation Degree Equal to 1 Sulfate Group Per Repetitive Unit 21.0 g of hyaluronic acid sodium salt of an extractive origin (500-730 KD) are dissolved in 1.5 l of water and the resulting solution is percolated through a glass column pre-filled with 450 cm$^3$ of Dowex resin in the form of TBA. The eluted solution of HA-TBA salt is collected and freeze-dried. 32.0 g of product are obtained, which are dissolved in 1.65 l of NMP; 40 g of PySO$_3$ are dispersed in 350 ml of NMP, and then added to the solution of HA. After 20 hours under mechanical stirring at a temperature of 25±1° C., the reaction is interrupted adding 0.5 volumes of water. The pH initially lower than 2.5, is brought to neutrality by the addition of NaOH (in solution at a concentration of 4 moles/l). The reaction raw product is isolated by precipitation by the addition of 3.5 volumes of methanol and washed with 3.5 volumes of a methanol/water mixture 8/2. The solid is re-dissolved and exhaustively dialyzed against water through a membrane with a cut-off of 12-14,000 Da. 22.5 g of product are obtained with a sulfation degree equal to 1.0 sulfate group per repetitive unit (yield=87%).

Example 8

Figure 1:
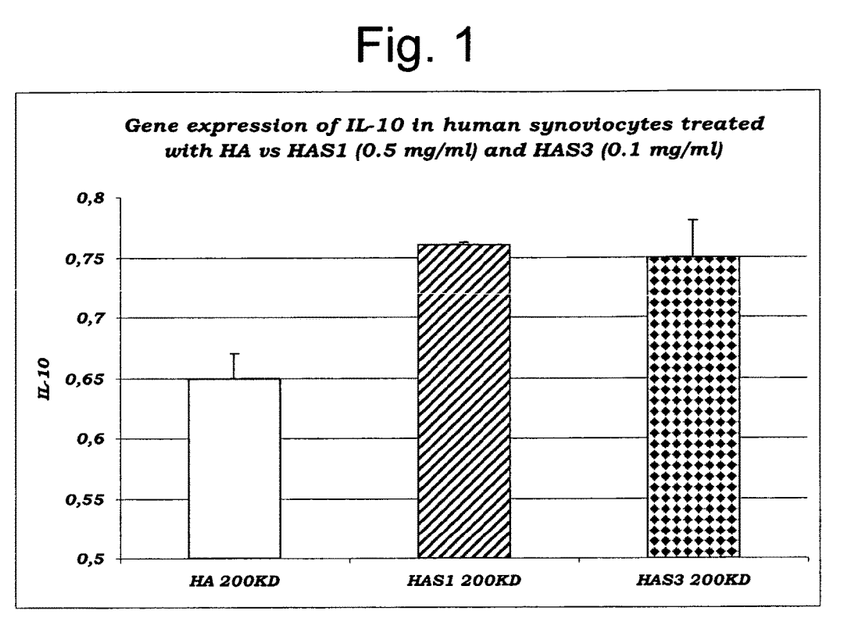
FIG. 1 shows the gene expression of IL-10 in human synoviocytes treated with HA, HAS1 or HAS3.
Figure 2:
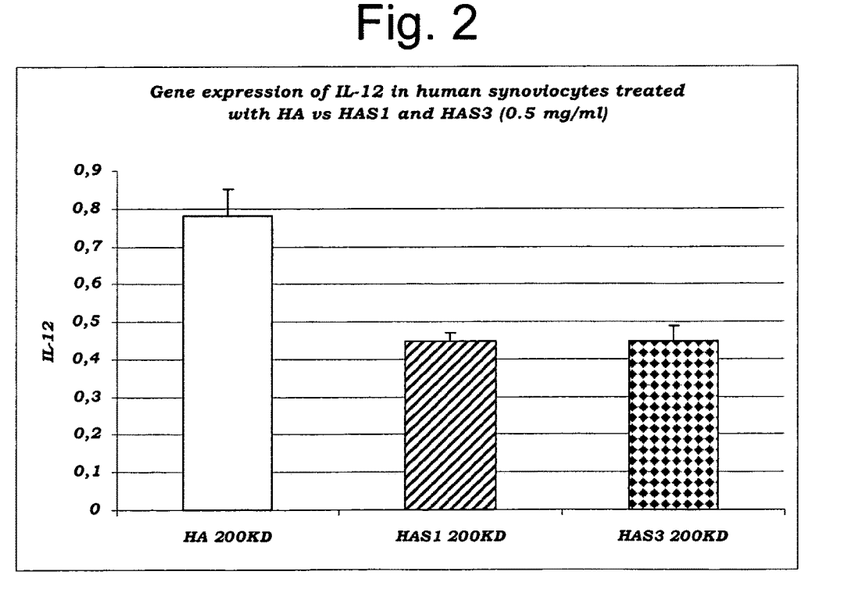
FIG. 2 shows the gene expression of IL-12 in human synoviocytes treated with HA, HAS1 or HAS3.

Evaluation of the Regulatory Effect of Has Degree 1 and Degree 3 on the Gene Expression of IL-10 and IL-12 in Human Synoviocytes Human synoviocytes previously expanded in vitro and maintained in a culture at 37° C. with a medium of DMEM containing 10% of FCS, were seeded at a concentration of 20,000 cells per well. Sulfated HA degree 1 (HAS1) and degree 3 (HAS3) prepared as described in Examples 1-3, were then added to the culture medium at concentrations of 0.1 and 0.5 mg/ml (for both samples), whereas the control treatment is represented by non-sulfated HA having an average molecular weight (MW) of 200 KD. After 3 days of treatment, the PCR Real Time was effected to evaluate the gene expression of IL-10 and IL-12: the cell RNA was extracted using the "Trizol" method, following the indications of the supplier (TRIZOL reagent, LIFE Technologies, GIBCO BRL). In short, the cells were lysed by the addition of 1.0 ml of Trizol and the total RNA was quantified by measuring its absorbance at 260 nm. The appropriate primers were selected for each gene to be amplified, using the software Primer3 (Roche Molecular Diagnostics, Pleasanton, Calif., USA). The gene expression was evaluated by means of PCR Real Time effected with a Rotor-gene TM5500 (Corbett research, Sydney, Australia). The PCR reactions were effected using primers at 300 nm and SYHR Green (Invitroge, Carlsbad, Calif., USA) at 40 cycles of 15 s at 95° C., and 1 min. at 60° C. The value of Fluorescence thresholds (CW was automatically determined by the software, evaluating an amplification coefficient for the genes studied between 92 and 110%. For each sample of cDNA, the gene expression value was expressed in terms of the ratio between the ct of the house keeping gene (i.e. the gene for the beta-Actin protein which represents the control gene as it is present in every cell and is not subjected to the influence of HAS) and the ct of the gene of interest (i.e. the gene for IL-10 and IL-12), consequently the house keeping ct/gene ct value is indicated in the axis of the ordinates, which therefore indicates the quantity of mRNA expressed by the gene which is being studied. The results obtained are expressed in FIGS. 1 and 2:

FIG. 1: the treatment of human synoviocytes with HAS1 and HAS3 caused a significant increase in the gene expression of the cytokine IL-10 vs the control treated with non-sulfated HA,

FIG. 2:

Also in this experiment, both sulfation degrees (degree 1 and degree 3) of HAS proved to be capable of significantly reducing the gene expression of IL-12, halving the synthesis of its mRNA vs the control treated with non-sulfated HA. The sulfated hyaluronic acid therefore proved to be:
  capable of stimulating the production of new mRNA for the synthesis of anti-inflammatory cytokines, thus increasing the defence capacity of the cell and consequently of the whole organism, vs those pathologies previously described in which IL-10 proved to be of fundamental importance for the resolution and/or improvement of diseases such as asthma, rheumatoid arthritis, arthrosis and all inflammations in which IL-10 is involved.
  effective in diminishing the synthesis of new mRNA of the highly pro-inflammatory cytokine IL-12, proving to be a valid anti-inflammatory agent capable of intervening on the expression of proteins involved in the pathogenesis of invalidating diseases such as psoriasis, arthritis and all those previously described.

Example 9

Inhibition of the Binding of TNF to its Receptor Expressed in Monocyte Lines: Evaluation of the Effectiveness of HAS Degree 1 and Degree 3 at Different MW Values These experiments were effected to evaluate the effectiveness of the samples tested (prepared according to Examples 1-4) on the capacity of inhibiting the binding of TNF to its receptor expressed by cells of the I.S. normally used in vitro for this type of experiment, carried out with iodinated cytokine components for an evaluation in Radioligand Binding assays.

The experimental procedure was effected as described in Baglioni C. et al., J Biol Chem, 1985, 260:13395-13397.

In short, the line of human histiocytes of the lymphoma U937 was used, with characteristics of monocytes sensitive to the cytotoxic activity of TNF, expressing its relative receptor. The cells were initially incubated with $^{125}$I-TNF 0.028 nM (carried in water) contemporaneously with the samples to be analyzed (at a concentration of 1 mg/ml which proved to be the lowest concentration which causes the maximum inhibition), in an incubation buffer consisting of 50 mM Tris-HCL pH 7.4, 0.5 mM EDTA, at 4° C. for 3 hours.

At the end of the incubation, the cells were centrifuged with dibutylphthalate/dinonylphthalate 2/1 and the pellet obtained was counted in a γ-counter.

Figure 3:
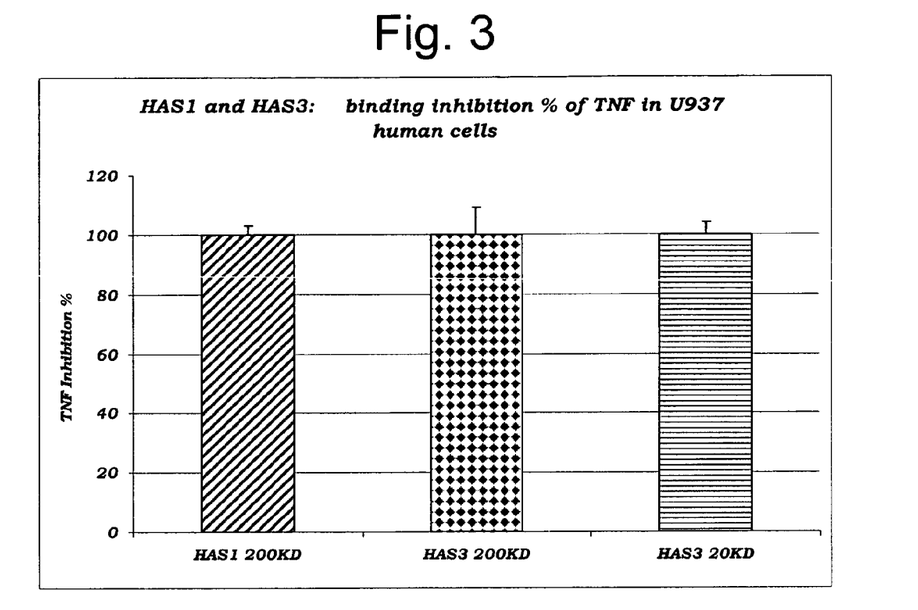
FIG. 3 shows binding inhibition percent of TNF with HA, HAS1 or HAS3.

The results obtained are expressed in FIG. 3:

The results obtained show the effectiveness of HAS in totally (100%) inhibiting the binding of TNF to its receptor, for both degree 1 and degree 3, with a medium and low MW. These results are of fundamental importance as they prove that the behaviour of the sulfated product is completely analogous to that of a monoclonal antibody specific for the TNF receptor, capable therefore of blocking its function. This receptor blockage consequently represents the most effective way of antagonizing the pro-inflammatory and tumoral effects of the TNF factor.

Example 10

Inhibition of the Binding of the Cytokine IL-1 to its Receptor Expressed in Fibroblast Lines: Evaluation of the Effectiveness of HAS Degree 3 at Different MW Values These experiments were effected to evaluate the effectiveness of the samples tested (prepared according to Examples 1-3 and 4) on the capacity of inhibiting the binding of IL-1 to its receptor expressed by 3T3 cells of mice, normally used in vitro for this type of experiment, carried out with iodinated cytokine components for an evaluation in Radioligand Binding assays.

The experimental procedure was effected as described in Chin J et al., J Exp Med, 1987, 165:70-86.

In short, the line of murine fibroblasts 3T3 was used, sensitive to the cytotoxic activity of IL-1, expressing its relative receptor. The cells were initially incubated with $^{125}$I-IL-1 10 pM (carried in water) contemporaneously with the samples to be analyzed (at a concentration of 1 mg/ml which proved to be the lowest concentration which causes the maximum inhibition), in an incubation buffer consisting of RPMI 1640 containing 20 mM HEPES pH 7.2 and 1% BSA, at 37° C. for 2 hours. At the end of the incubation, the cells were washed with phosphate buffer, then dissolved in 2.5 M of NaOH and counted in a γ-counter.

Figure 4:
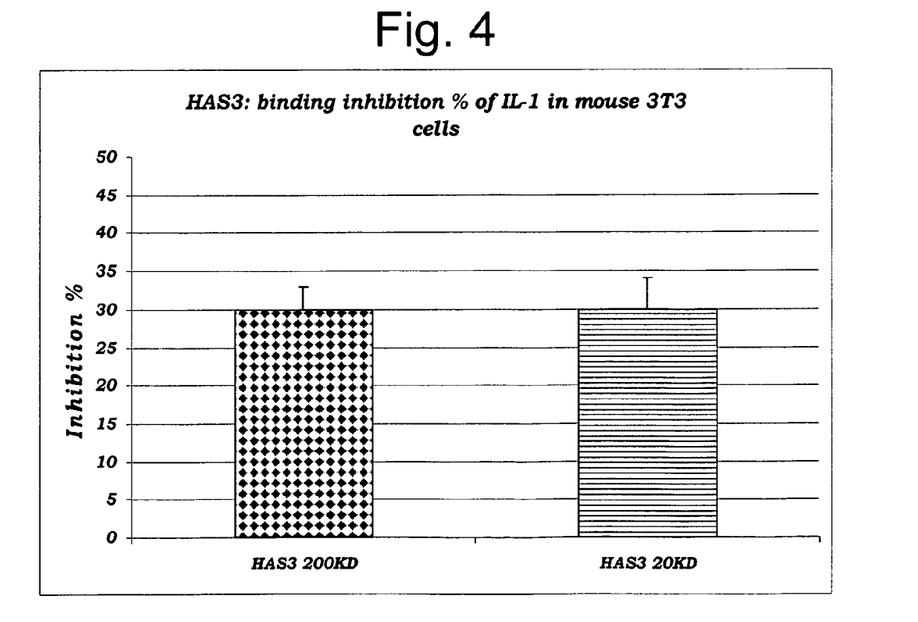
FIG. 4 shows HAS3 binding inhibition percent of IL-1.

The results obtained are expressed in FIG. 4:

The results obtained show the effectiveness of HAS (with both medium and low MW) in inhibiting the binding of IL-1 to its receptor by 30%. These results are extremely significant as they prove that the behaviour of the sulfated product is completely analogous to that of a monoclonal antibody specific for the receptor of the cytokine in question, capable therefore of blocking its function. This receptor blockage represents the most effective way of antagonizing the pro-inflammatory and tumoral effects of IL-1, as previously described.

Example 11

Inhibition of the Binding of the Cytokine IL-6 to its Receptor Expressed in Human Myeloma Cells: Evaluation of the Effectiveness of HAS Degree 3 at Different MW Values These experiments were effected to evaluate the effectiveness of the samples tested (prepared according to Examples 1-3 and 4) on the capacity of inhibiting the binding of IL-6 to its receptor expressed in human myeloma U266, normally used in vitro for this type of experiment, carried out with iodinated cytokine components for an evaluation in Radioligand Binding assays.

The experimental procedure was effected as described in Taga T. et al., J Exp Med, 1987, 166:967-981.

In short, the line of human myeloma U266 was used, sensitive to the cytotoxic activity of IL-6, expressing its relative receptor. The cells were initially incubated with $^{125}$I-IL-6 0.08 nM (carried in water) contemporaneously with the samples to be analyzed (at a concentration of 1 mg/ml which proved to be the lowest concentration which causes the maximum inhibition), in an incubation buffer consisting of RPMI 1640 containing 25 mM HEPES pH 7.1 and 10% BSA, at 4° C. for 16 hours. At the end of the incubation, the cells were washed with phosphate buffer, centrifuged at 9,000 rpm and the pellet counted in a γ-counter.

Figure 5:
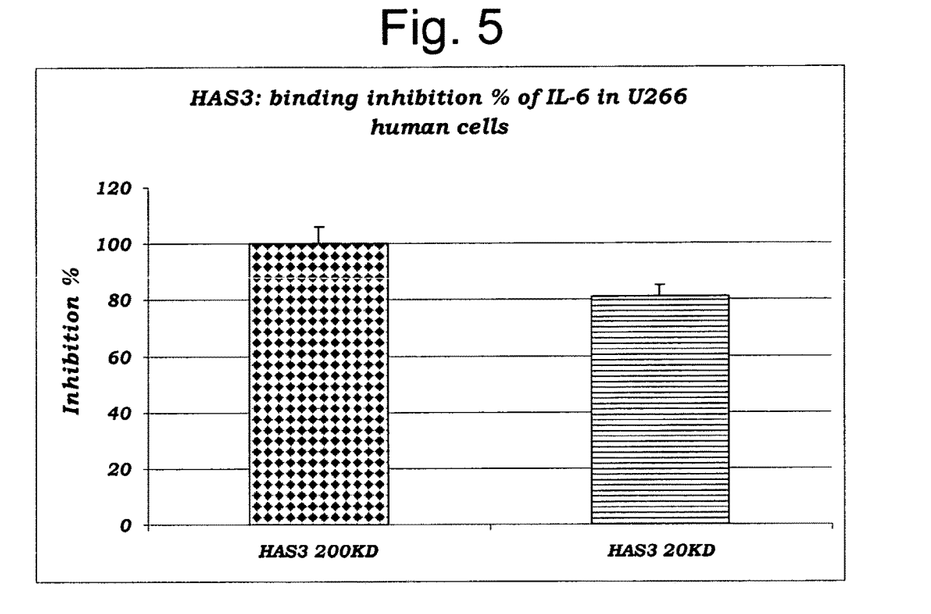
FIG. 5 shows HAS3 binding inhibition percent of IL-6.
Figure 6:
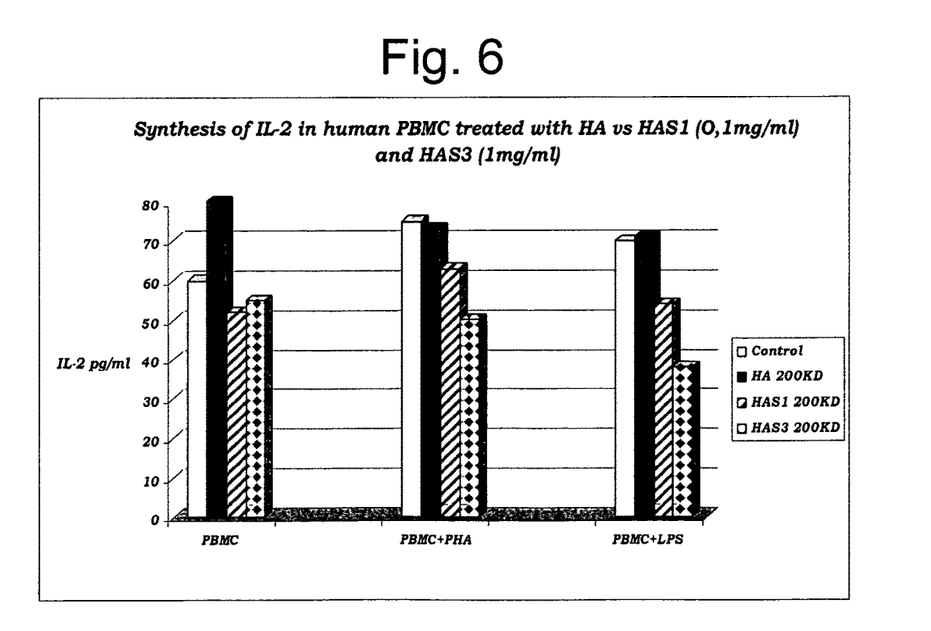
FIG. 6 shows the synthesis of IL-2 in human PBMC treated with HA, HAS1 or HAS3.
Figure 7:
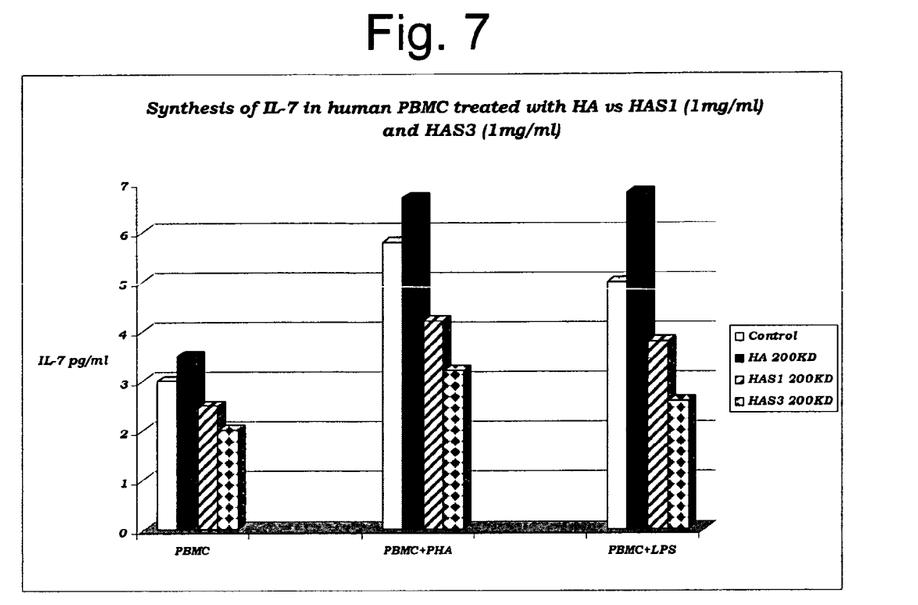
FIG. 7 shows the synthesis of IL-7 in human PBMC treated with HA, HAS1 or HAS3.
Figure 8:
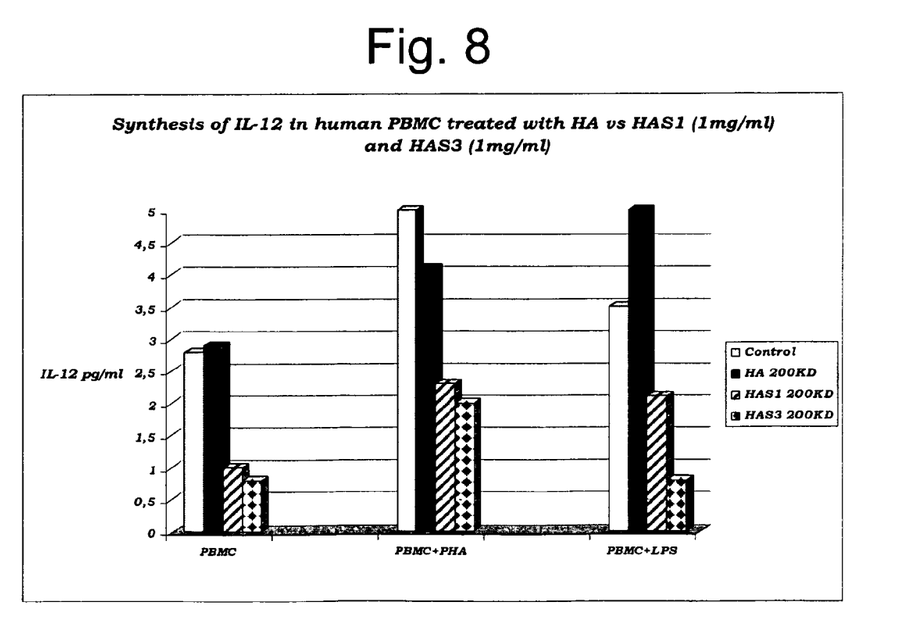
FIG. 8 shows the synthesis of IL-12 in human PBMC treated with HA, HAS1 or HAS3.

The results obtained are expressed in FIG. 5:

The results obtained show the effectiveness of HAS, with both medium and low MW, in inhibiting the binding of IL-6 to its receptor by up to 100%. These results consequently prove that the behaviour of the sulfated product, also in this case, is completely analogous to that of a monoclonal antibody specific for the receptor of the cytokine in question, capable therefore of blocking its function. This receptor blockage represents the most effective way of blocking the pro-inflammatory effects of IL-6.

Example 12

Evaluation of the Inhibitory Effect of HAS Degree 1 and Degree 3 on the Protein Synthesis of the Cytokines IL-2, IL-7, IL-10 and IL-12 in Human PBMC For these experimentations, mononucleate cells of human peripheral blood (PBMC) were adopted, deriving from many different donors for evaluating the effect of HAS on the production of the cytokines listed above, using:
  non-sulfated HA (average MW: 200 KD),
  HAS1 and HAS3 (prepared as described in Examples 1-3 (average MW: 200 KD).

The separation of the PBMC (Boyum A., Scand J Clin Lab Invest 21 Suppl, 1968, 97:77-89) was effected using the product Ficoll-Paque PLUS (GE Healthcare) and following the protocol indicated by the supplier. At day zero 100,000 cells were seeded per well (using plates with 96 wells) in 200 μl of medium RPMI 1640, to which 10% of fetal bovine serum, HEPES 10 mM, Glutamine 2 mM, 1% Penicillin-Streptomycin 100 U/ml, had been added. The effect of all the samples was evaluated on non-treated PBMC with agents which stimulate the synthesis of cytokines, or stimulated with Lipopolysaccharide LPS (10 µg/ml) (highly pro-inflammatory) or with Phytohemagglutinin PHA (10 µg/ml) (a substance capable of stimulating the lymphocytes to divide themselves), both agents capable of stimulating the synthesis of cytokines. The cells were treated separately with the three compounds at a concentration of 0.1 mg/ml or 1 mg/ml. After 24 hours of incubation at 37° C. (5% $CO_2$), 100 µl of supernatant were taken from each well in order to analyze the production of IL-2, IL-7, IL-10 and IL-12.

The quantification of the inflammation mediators was effected by means of the SearchLight® technology, using a Custom Human 9-Plex Array plate following the protocol indicated by the supplier in the technical card.

The results obtained are expressed in FIGS. 6-9: These graphs clearly show that HAS degree 1 and degree 3 are capable of significantly reducing the synthesis of IL-2, IL-7 and IL-12 on the part of monocytes, both when the cells are not stimulated and also when, on the contrary, they are stimulated by specific and powerful inflammatory factors and/or mitogens. HAS therefore proves to be a molecule with precise pharmacological characteristics, capable of modulating/regulating the synthesis of cytokines with a marked anti-inflammatory activity, both in situations where an immune response is not stimulated, and in particular inflammatory stress events in which the immune cell responds by producing a cytokine cascade and, above all, in this case, the data presented reveal a greater HAS modulating effect.

Figure 9:
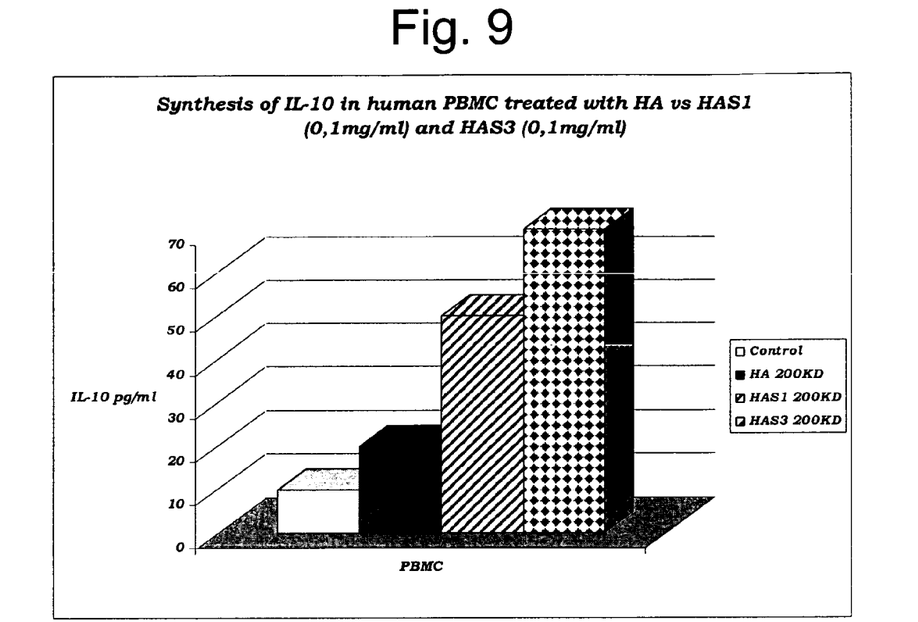
FIG. 9 shows the synthesis of IL-10 in human PBMC treated with HA, HAS1 or HAS3.

FIG. 9, on the other hand, confirms the evident stimulus for the production of IL-10 also for cells such as human monocytes (besides synoviocytes) belonging to the Immune System. It is consequently again confirmed that HAS is capable of modulating the synthesis of cytokines, stimulating those which are anti-inflammatory and inhibiting the synthesis of pro-inflammatory cytokines.

Example 13

Evaluation of the Antiviral Action of HAS Degree 1 and Degree 3 Vs HA-NS

HIV-1 ($III_B$) and HIV-2 (ROD) Virus

The activity of the samples tested was determined by evaluating the inhibition of the cytopathogenicity determined by the HIV-1 virus (obtained from T lymphocytes infected by the type $III_B$ virus) and HIV-2 virus (obtained from T lymphocytes infected by the type ROD virus) in MT4 cells. The experimental procedure was effected as described in Baba M. et al., ANTIMICROB. AGENTS CHEMOTHER., 1988, 32:1742-1745.

In short, human T lymphocytes called MT-4 infected by the HIV-1 virus strain $III_B$ and HIV-2 strain ROD, were used for this assay, Different concentrations of the samples tested were adopted for this test, using dextran-sulfate as positive control, a polysaccharide known for its capacity of inhibiting different types of viruses. The samples tested were:
1. HS-NS1: sulfated hyaluronic acid prepared by sulfation of the glucosamine after deacetylation, degree 1 (EP0971961), to compare it with
2. HAS1: sulfated hyaluronic acid only in its hydroxyl groups, degree 1, and
3. HAS3: sulfated hyaluronic acid only in its hydroxyl groups, degree 3, prepared as described in Examples 1-3 (all the samples with average MW: 200 KD).

The antiviral activity of the samples tested is expressed as the minimum concentration required for inhibiting the cytopathogenicity of the virus by 50%: IC50. The cells were treated with various concentrations of the above samples added immediately after the infection with infective doses of HIV. After 5 days at 37° C., the number of vital cells is determined with the MTT test: tetrazole salt subjected to redox reaction only by the mitochondrial enzymes of vital cells. The infected and non-treated cells lose the progressive capacity of transforming the tetrazole salt to formazans, consequently, if these cells keep this capacity intact after infection and treatment, this means that this treatment has inhibited the viral action, thus blocking the pathogenicity of the virus (Dezinot F. et al., J. Immunol. Methods, 1986, 22(89): 271-277).

Figure 10:
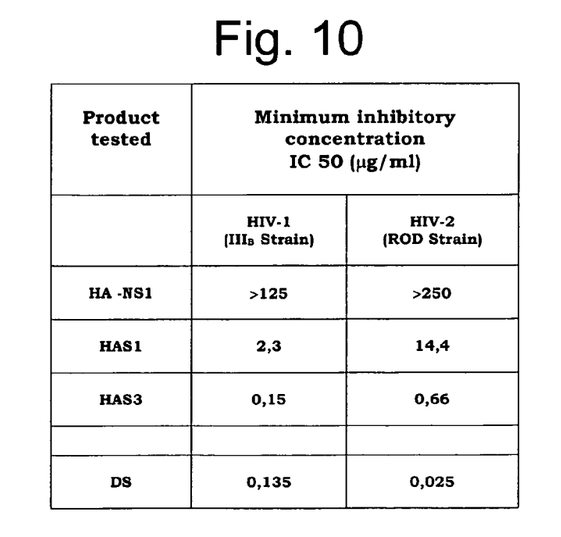
FIG. 10 shows the antiviral activity against HIV strains of HA-NS1, HAS1, and HAS3.

The results obtained are expressed in FIG. 10:

The results obtained demonstrate the effectiveness of HAS (both degree 1 and degree 3) in inhibiting the viral replication of the virus HIV 1 and 2, in a way which is completely comparable to the positive control (represented by the polysaccharide dextran-sulfate). The experimentation also demonstrated that not all sulfated hyaluronic acids known in the state of the art act effectively vs the replication of the virus studied, as the Applicant has proved that only the HAS whose sulfation has taken place with respect to its hydroxyl groups proves to be active in its powerful antiviral action as HA-NS is not effective in blocking the viral cytopathogenicity.

Herpes Simplex Virus-1, Herpes Simplex Virus-2, Vesicular Stomatitis Virus

The activity of the samples tested was determined by evaluating the inhibition of the cytopathogenicity caused by the virus of Herpes Simplex Virus-1, (HSV-1: KOS, F and McIntyre strain) and by the virus of Herpes Simplex Virus-2, (HSV-2: G, 196 and Lyons strain) in $E_6SM$ fibroblast cells which derive from muscular/embryonic skin tissue. Furthermore, the anti-viral activity was tested again vs $E_6SM$ cells infected by the virus of vesicular stomatitis (Vesicular stomatitis virus: VSV). HSV-1 is the virus which preferentially infects the oral mucous, whereas HSV-2 attacks the genital mucous. The experimental procedure was effected as described in Baba M. et al., ANTIMICROB. AGENTS CHEMOTHER., 1988, 32:1742-1745.

In short, confluent cell cultures were exposed to infective doses of the viruses listed above in the presence of the samples HS-NS1 (EP0971961), HAS1 and HAS3 prepared as described in Example 1 and 2 (all the samples with an average MW: 200 KD). After an incubation period of 1 h at 37° C., the culture medium was substituted with fresh medium only containing the samples to be tested. The cytopathogenicity of the virus was tested on the $2^{nd}$ day of incubation. The measurement of the inhibition of the viral cytopathogenicity was evaluated by determining the inhibition of the synthesis of DNA and RNA in the "infected" cells and subjected to treatment as indicated above: the cells were seeded in micro-wells in a culture medium containing different concentrations of the samples to be tested with 2.5 µCi of 3H-thymidine and 3H-uridine per ml. After 16 h at 37° C., the cells were treated with Trichloroacetic acid, washed in ethanol, left to dry and counted in 7.5 ml of liquid by scintillation. The antiviral activity of the samples tested is expressed as the minimum concentration required for inhibiting the cytopathogenicity of the virus by 50%: IC50. Furthermore, in order to also evaluate the cytotoxicity of the samples tested, the minimum concentrations necessary for causing morphological damage (observable with an optical microscope) to the cells used, were determined. The comparison was effected vs dextran-sulfate and the drug Acyclovir (both molecules with a known antiviral effectiveness, therefore used as positive control).

Figure 11:
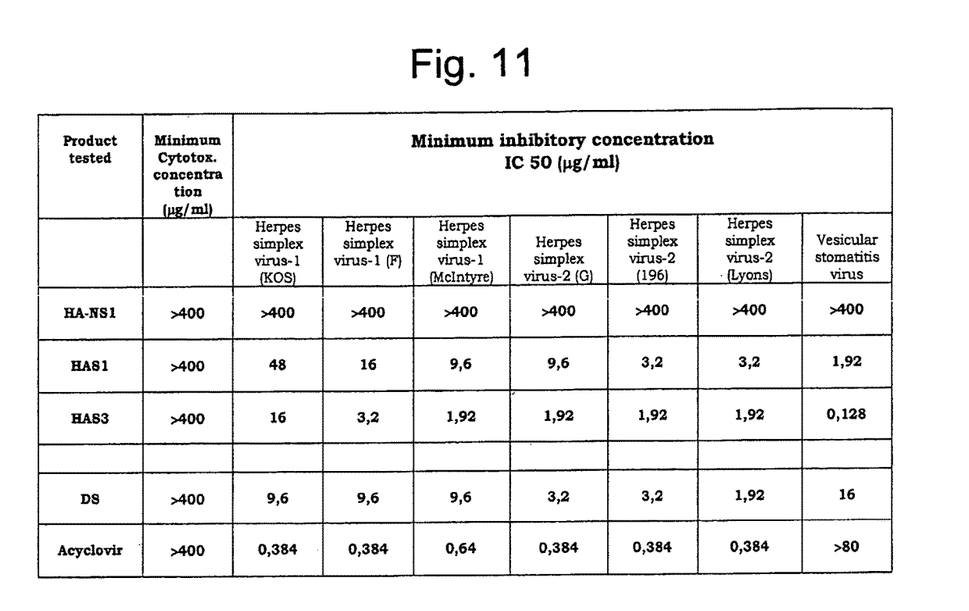
FIG. 11 shows the antiviral activity against various herpes simplex strains and vesicular stomatitis virus of HA-NS1, HAS1, and HAS3.

The results obtained are expressed in FIG. 11:

The experimental data confirm what was seen for HIV, i.e. the powerful antiviral action of both HAS1 and HAS3: a comparison between HA-NS1 and HAS1 shows that not all sulfated hyaluronic acids are equivalent as HA-NS1 did not prove to be active, and this difference in efficacy does not depend on the molecular weight or the sulfation degree of hyaluronic acid, it therefore lies in the very structure of HA-NS1 vs HAS1, i.e. on the sulfation. HAS in fact shows an efficacy equal to that of dextran-sulfate and comparable to that of acyclovir, a reference drug for the treatment of Herpes Simplex. Furthermore, it should be pointed out that acyclovir is inactive vs VSV, whereas HAS degree 1 and 3 has a very powerful antiviral activity vs VSV.

All the samples tested are non-cytotoxic towards the host cell, the minimum cytotoxic concentration obtained is in fact equal to that of the reference drugs normally used in clinical practice for the treatment of Herpes, and proved to be on an average 100 times higher than that proved active in the inhibition of the viral replication.

Cytomegalovirus

Figure 12:
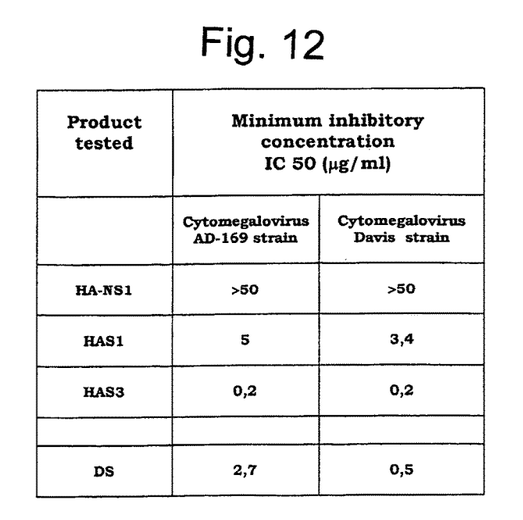
FIG. 12 shows the antiviral activity against cytomegalovirus strains of HA-NS1, HAS1, and HAS3.

The activity of the samples tested was determined by evaluating the inhibition of the cytopathogenicity determined by Cytomegalovirus (CMV: AD-169 and Davis strain) using the previous protocol. The antiviral activity was tested vs HEL cells (pulmonary embryonic cells) and was expressed as the concentration required for inhibiting the number of plaques formed by the above virus by 50%. The results obtained are expressed in FIG. 12:

the table indicates the clear and significant positive result obtained for both HAS1 and HAS3 which again confirms them as effective antiviral agents. Also in this case, HA-NS1 did not prove to be active in inhibiting the proliferation of the virus, confirming the absolute diversity between the two types of degree 1 sulfated product in having an antiviral capacity.

Example 14

Preparation of a Formulation in the Form of a Solution for Inhalations Containing Sulfated Hyaluronic Acid Degree 1

40 mg (or 20 mg if the HAS has a MW of 500-730 KD) of sulfated hyaluronic acid degree 1, having a low or medium MW, are introduced into a 50 ml glass flask, after which 15 ml of PBS 0.2M at sterile pH 7.4, are added. The mixture is subjected to stirring for about 30 minutes, until the complete dissolution of the powder. When the complete dissolution has been obtained, 2 ml of glycol propylene and further PBS 0.2M at sterile pH 7.4 are added until the total volume of 20 ml is reached. The solution is maintained under stirring for a few minutes.

Example 15

Preparation of a Formulation in the Form of a Solution for Inhalations Containing Sulfated Hyaluronic Acid Degree 3

100 mg of sulfated hyaluronic acid degree 3 obtained from HA 200 KD are introduced into a 50 ml glass flask, after which 15 ml of PBS 0.2M at sterile pH 7.4, are added. The mixture is subjected to stirring for about 30 minutes, until the complete dissolution of the powder. When the complete dissolution has been obtained, 2 ml of glycol propylene and further PBS 0.2M at sterile pH 7.4 are added until the total volume of 20 ml is reached. The solution is maintained under stirring for a few minutes.

Example 16

Preparation of a Formulation in the Form of an Injectable Solution for Intra-Articular Use Containing Sulfated Hyaluronic Acid Degree 1

500 mg of sulfated hyaluronic acid degree 1 obtained from HA with a MW of 500-730 KD are introduced into a 50 ml glass flask, and PBS 0.2M at sterile pH 7.4, is then added until the total volume of 20 ml is reached. The mixture is subjected to stirring for about 60 minutes, until the complete dissolution of the powder.

Example 17

Preparation of a Formulation in the Form of a Hydrophilic GEL Containing HAS, HA and CMC Methyl- and propyl-parabene are dissolved in purified water at 80° C. After cooling the solution to room temperature, sodium hyaluronate is added under stirring until dissolution followed by HAS1 (or HAS3), maintaining the stirring until complete dissolution. Glycerol and propylene glycol are then added under stirring until complete dissolution. Sodium carboxymethylcellulose (CMC) is finally added and the mixture is mixed until a gelified solution is obtained.

Example 18

Preparation of a Formulation in the Form of a Hydrophilic GEL for Mucosal Use (without Preservatives) Containing HAS and HA Sodium hyaluronate is dissolved under stirring, and then HAS1 (or HAS3) in a quantity of water of about 90% of that envisaged in the formula. Propylene glycol, Symdiol 68 are added followed by MP Diol Glycol and the mixture is mixed until the complete dissolution of the various components. Carbomer 974P is subsequently added and the stirring is maintained until the homogeneous dispersion of the latter. Beads of sodium hydroxide are dissolved in the remaining 10% of water and this solution is added to the that previously obtained, to obtain the gelification of the aqueous phase.

Example 19

Preparation of a Formulation in the Form of a Lipstick Containing HAS and HA

The correct quantity of liquid paraffin indicated in the manufacturing formula is charged into a suitable container. It is heated to 88-92° C. and white soft paraffin, hard paraffin, white beeswax, ceresin, arlacel are then added under stirring, the stirring is maintained until the complete melting of the various components. All-rac-a-tocopheryl acetate, allantoine, butylhydroxytoluene, propyl p-hydroxybenzoate are then incorporated and the mixture is mixed until complete dissolution, maintaining the mass at 88-92° C.

The quantity of purified water envisaged in the formula is charged separately into a suitable container, sodium hyaluronate, HAS1 (o HAS3) are then added under stirring until complete dissolution, followed by Disodium Edetate maintaining the stirring until dissolution.

The aqueous phase is transferred under stirring to the container containing the molten mass, maintaining the system at 88-92° C. and the stirring until a limpid solution is obtained. The two aromatizing agents are then added under stirring and the mixture is mixed for 10'. The molten mass is poured into moulds and is immediately cooled to T<0° C. until solid sticks are obtained.

Example 20

Preparation of a Formulation in the Form of Vaginal OVULES containing HAS and HA The gelatine is allowed to swell in 70% of purified water at 85° C.; sodium hyaluronate and HAS1 (or HAS3) are dissolved in the remaining quantity of water and this solution is mixed with the glycerine brought to the same temperature. The glycerine solution is added to the swollen gelatine solution and the stirring is maintained until the complete dissolution of the gelatine. The mass is poured into moulds and cooled to T<0° C. until solid ovules are obtained.

Example 21

Preparation of a Formulation in the Form of a Hydrophilic Cream Containing HAS and HA The oil phase is prepared by melting liquid paraffin, stearic acid and Tefose 1500 under stirring at 50° C. The aqueous phase is prepared separately by the initial dissolution at 80° C. of methyl-parabene and subsequent cooling to room temperature and the incorporation of glycerol, sodium hyaluronate and subsequently HAS1 (or HAS3) under stirring until the complete dissolution of the various components.

The aqueous phase is joined to the oil phase and emulsification is effected, the emulsion 0/A obtained is cooled under stirring to room temperature.

Example 22

Preparation of a Formulation in the Form of an Ointment Containing HAS

The base ointment is prepared by melting light liquid paraffin and white Vaseline under stirring at 70° C. After cooling to room temperature, HAS1 (or HAS3) is incorporated under stirring and the mixture is mixed until a homogeneous suspension is obtained.

Example 23

Preparation of a Formulation in the Form of Capsules (Hard Gelatine) Containing HAS HAS1 (HAS3) is mixed with calcium phosphate, magnesium stearate and silica by progressive dilution. The capsules are then filled.

Example 24

Preparation of a Formulation in the Form of Tablets Containing HAS

HAS1 (or HAS3) is subjected to wet granulation in a fluid bed with a ligand solution consisting of water and about 70% of the total quantity of sodium CMC. The granulate obtained is subjected to sieving on an 0.8 mm net.

The remaining ingredients (calcium phosphate, microcrystalline cellulose, sodium CMC and silica) are mixed and sieved on an 0.8 mm net.

The granulate previously obtained is mixed with the mixture consisting of the remaining ingredients (extragranules), and is finally mixed with magnesium stearate (previously sieved on an 0.8 mm net), followed by compression.

Example 25

Preparation of a Formulation in the Form of an Injective Solution Containing HAS After the preparation (at room temperature) of a physiological solution buffered at pH 6.4-7.2, lactose is dissolved under stirring and finally HAS1 or HAS3. The solution thus obtained is filtered on 0.22 microns.

TABLE

| HYDROPHILIC GEL (Example 17) | |
|---|---|
| Components | Quantity (mg/1 g of hydrogel) |
| HAS1 (HAS3) | 40 mg (10 mg) |
| CMC | 20 mg |
| Glycerol | 100 mg |
| Propylene Glycol | 66.75 mg |
| Sodium Hyaluronate | 2 mg |
| Methyl p-hydroxybenzoate | 2 mg |
| Propyl p-hydroxybenzoate | 0.2 mg |
| Purified Water | q.s to 1 g |

| HYDROPHILIC GEL for mucosal use (Example 18) | |
|---|---|
| Components | Quantity (mg/1 g of hydrogel) |
| HAS1 (HAS3) | 10 mg |
| Carbomer 974P | 15 mg |
| Propylene Glycol | 100 mg |
| Sodium Hydroxyde | 0.33 mg |
| Sodium Hyaluronate | 2 mg |
| MP-Diol Glycol | 37.5 mg |
| SymDiol 68 | 90 mg |
| Purified Water | q.s to 1 g |

| LIPSTICK (Example 19) | |
|---|---|
| Components | Quantity (mg/1 g lipstick) |
| HAS1 (HAS3) | 30 mg (10 mg) |
| Liquid Paraffin | 253.2 mg |
| White Soft Paraffin | 326.2 mg |
| Hard Paraffin | 144.3 mg |
| Beeswax white | 96 mg |
| Ceresin | 28.2 mg |
| Arlacel 582 | 95.8 mg |
| Sodium Hyaluronate | 2 mg |
| Allantoin | 1.1 mg |
| all-rac-a Tocopheryl Acetate | 1.1 mg |
| Propyl p-hydroxybenzoate | 0.4 mg |
| Butylhydroxytoluene | 0.4 mg |
| Purified Water | 19.2 mg |
| Disodium Edetate | 1.1 mg |
| Vanilla Flavour | 0.5 mg |
| Sweet Flavour | 0.5 mg |

| VAGINAL OVULES (Example 20) | |
|---|---|
| Components | Quantity (mg/1 g of ovule) |
| HAS1 (HAS3) | 10 mg |
| Glycerin | 580 |
| Gelatin | 200 |
| Sodium Hyaluronate | 2 |
| Purified Water | q.s to 1 g |

| HYDROPHILIC CREAM (Emulsion O/A) (Example 21) | |
|---|---|
| Components | Quantity mg/1 g of cream) |
| HAS1 (HAS3) | 10 mg |
| Tefose 1500 | 110 mg |
| Glycerol | 80 mg |
| Stearic Acid | 33 mg |
| Sodium Hyaluronate | 2 mg |
| Liquid Paraffin | 40 mg |

TABLE-continued

| | |
|---|---|
| Methyl p-hydroxybenzoate | 1 mg |
| Purified Water | q.s to 1g |

OINTMENT (Example 22)

| Components | Quantity (mg/1 g of ointment) |
|---|---|
| HAS1 (HAS3) | 20 mg |
| Light Liquid Paraffin | 200 mg |
| White Petrolatum | q.s to 1 g |

CAPSULES (Hard Gelatine) (Example 23)

| Components | Quantity (mg/capsule) |
|---|---|
| HAS-1 (HAS3) | 80 mg (40 mg) |
| Calcium Phosphate | 256 mg |
| Magnesium Stearate | 7 mg |
| Silica | 7 mg |

TABLETS (Example 24)

| Components | Quantity (mg/tablet) |
|---|---|
| HAS-1 (HAS-3) | 120 mg |
| Calcium Phosphate | 200 |
| Microcrystalline cellulose | 185 |
| Sodium Carboxymethylcellulose | 10 |
| Magnesium Stearate | 10 |
| Silica | 15 |

INJECTIVE FORMULATIONS (Example 25)

| Components | Quantity (mg/ml of sol) |
|---|---|
| HAS-3 | 50 mg |
| Lactose | 0.93 mg |

TABLE-continued

| | |
|---|---|
| Potassium Phosphate Dibasic | 0.36 |
| Potassium Phosphate Monobasic | 0.23 |
| Sodium Chloride | 9 |

The description being thus described, these methods can obviously be modified in various ways. These modifications should not be considered as diverging from the spirit and perspectives of the invention and all the modifications which can appear evident to a skilled person in the field are included in the scope of the following claims.

The invention claimed is:

1. A method for stimulating the synthesis of IL-10 in a patient in the treatment of dermatitis wherein said patient has an IL-10 deficit; comprising administering to a patient in need thereof as the only active agent sulphated hyaluronic acid (HAS) being prepared starting from a HA having a molecular weight within one of the following ranges (a) 150,000 to 250,000 Da and (b) 500,000 to 750,000 Da, and a sulphation degree equal to 1 or 3.

2. The method according to claim 1, wherein said administration is systemic administration.

3. The method according to claim 1, wherein said administration is topical or inhalation administration.

4. A method for stimulating the synthesis of IL-10 in a patient in the treatment of dermatitis wherein said patient has an IL-10 deficit; comprising administering to a patient in need thereof an active agent comprising sulphated hyaluronic acid (HAS) being prepared starting from a HA having a molecular weight within one of the following ranges (a) 150,000 to 250,000 Da and (b) 500,000 to 750,000 Da, and a sulphation degree equal to 1.

* * * * *